United States Patent
Wu et al.

(10) Patent No.: US 11,083,383 B1
(45) Date of Patent: Aug. 10, 2021

(54) PORTABLE ELECTROCARDIOGRAM DEVICE

(71) Applicant: Apple Inc., Cupertino, CA (US)

(72) Inventors: Chia Chi Wu, Taipei (TW);
Sheng-Yang Tsui, Taipei (TW); Shu Yu Lin, Shanghai (CN)

(73) Assignee: APPLE INC., Cupertino, CA (US)

( * ) Notice: Subject to any disclaimer, the term of this patent is extended or adjusted under 35 U.S.C. 154(b) by 98 days.

(21) Appl. No.: 16/128,044

(22) Filed: Sep. 11, 2018

Related U.S. Application Data (60) Provisional application No. 62/562,980, filed on Sep. 25, 2017.

(51) Int. Cl.
| | |
|---|---|
| *A61B 5/024* | (2006.01) |
| *A61B 5/00* | (2006.01) |
| *A61B 5/316* | (2021.01) |
| *A61B 5/25* | (2021.01) |
| *A61B 5/30* | (2021.01) |

(52) U.S. Cl.
CPC ........ *A61B 5/02438* (2013.01); *A61B 5/0006* (2013.01); *A61B 5/316* (2021.01); *A61B 5/6824* (2013.01); *A61B 5/0022* (2013.01); *A61B 5/25* (2021.01); *A61B 5/30* (2021.01); *A61B 5/681* (2013.01); *A61B 5/6831* (2013.01); *A61B 5/7203* (2013.01); *A61B 5/7225* (2013.01)

(58) Field of Classification Search
CPC .............. A61B 5/02438; A61B 5/0006; A61B 5/04017; A61B 5/6824; A61B 5/0022; A61B 5/0408; A61B 5/0428; A61B 5/681; A61B 5/6831; A61B 5/7203; A61B 5/7225
See application file for complete search history.

(56) References Cited

U.S. PATENT DOCUMENTS

| | | | |
|---|---|---|---|
| 9,603,542 B2 | 3/2017 | Veen et al. | |
| 2002/0007126 A1* | 1/2002 | Nissila | A61B 5/04085 600/509 |
| 2007/0100666 A1* | 5/2007 | Stivoric | A61B 5/01 705/3 |
| 2015/0182170 A1 | 7/2015 | Zdeblick et al. | |
| 2015/0272483 A1 | 10/2015 | Etemad et al. | |
| 2018/0126175 A1* | 5/2018 | Seitz | H01G 4/35 |

* cited by examiner

*Primary Examiner* — Catherine M Voorhees
*Assistant Examiner* — Roland Dinga
(74) *Attorney, Agent, or Firm* — Dorsey & Whitney LLP (57) ABSTRACT

Cardiac monitor devices are described. An exemplary cardiac monitor device can take the form of an armband that can be worn by a user. The cardiac monitor device can be paired with an electronic device so that the user can access information of his or her heart activity. In one embodiment, the cardiac monitor device can include a body that can be worn at a limb of the user. The body can carry different electronic components. The electronic components can include an electrode configured to come into contact with a location of the limb and configured to measure a first electrical potential at the location. The electronic components can also include an antenna configured to capacitively couple with the body of the user to generate a second electrical potential. The electronic components can further include an amplifier configured to amplify the potential difference.

20 Claims, 11 Drawing Sheets

PORTABLE ELECTROCARDIOGRAM DEVICE

CROSS-REFERENCE TO RELATED APPLICATIONS

The present application claims the benefit of U.S. Provisional Application No. 62/562,980, entitled "PORTABLE ELECTROCARDIOGRAM DEVICE," filed Sep. 25, 2017, which is incorporated herein by reference in its entirety for all purposes.

FIELD

Described embodiments can relate to portable electrocardiogram devices. More specifically, described embodiments can relate to portable electrocardiogram devices that are wearable and can include an antenna.

BACKGROUND

Cardiac electric fields result in cardiac potentials that can be sensed through the body surface of a user using electrodes. By monitoring the electric fields of a heart, the activities of the heart can be monitored. Conventionally, electrocardiogram information can be constructed by attaching two electrodes at the user's body to complete an electrical circuit. In more advanced medical devices, multiple electrodes are used to monitor the activities of the heart from different angles. Since multiple electrodes are attached to the user's body, the movement of the user is often severely limited. As a result, a continuous monitor of cardiac electric fields in a prolonged period is normally not feasible outside of the hospital setting.

SUMMARY

This paper describes various embodiments of cardiac monitor devices and systems.

According to one embodiment, a wearable device for detecting electrical activities of a heart of a user is described. The device can include a housing configured to be in contact with skin of the user when the wearable device is worn. The housing can carry an electrode configured to come into contact with a location of the skin and configured to measure a reference electrical potential at the location. The housing can also carry an antenna configured to be positioned across an air gap from a body of the user so that the antenna can be capacitively coupled with the body to generate a second electrical potential. The housing can further carry an amplifier configured to determine a potential difference between the reference electrical potential and the second electrical potential. The potential difference can represent the electrical activities of the heart. The housing can further include an output configured to transmit signals carrying information of the potential difference to an external circuit.

According to another embodiment, a portable electronic device that can present electrocardiographic information of a heart of a user is described. The portable electronic device can include a processor that can issue commands to control a cardiac monitor device that is separated from the portable electronic device. The cardiac monitor device can monitor electrical activities of the heart through capacitive coupling between an antenna of the cardiac monitor device and a body of the user. The portable electronic device can also include a wireless transceiver capable of transmitting the commands to the cardiac monitor device and receiving signals from the cardiac monitor device. The portable electronic device can further include a display assembly that can present the electrical activities of the heart as visual content in a form of electrocardiography based on the signals.

According to yet another embodiment, a system for monitoring electrical activities of a heart of a user is described. The system can include an electrode configured to come into contact with a location of skin of an upper arm of the user. The system can also include an antenna configured to be positioned across an air gap from a body of the user so that the antenna can be capacitively coupled with the body. The system can also include a processor that can generate a signal representing a potential difference between the electrode and the antenna. The potential difference can represent the electrical activities of the heart. The system can further include a display assembly controlled by the processor. The display assembly can present the signal as visual content.

Other aspects and advantages of the invention will become apparent from the following detailed description taken in conjunction with the accompanying drawings which illustrate, by way of example, the principles of the described embodiments.

BRIEF DESCRIPTION OF THE DRAWINGS

The disclosure will be readily understood by the following detailed description in conjunction with the accompanying drawings, wherein like reference numerals designate like structural elements, and in which.

Those skilled in the art will appreciate and understand that, according to common practice, various features of the drawings discussed below are not necessarily drawn to scale, and that dimensions of various features and elements of the drawings can be expanded or reduced to more clearly illustrate the embodiments of the present invention described herein.

DETAILED DESCRIPTION

Representative applications of methods and apparatus according to the present application are described in this section. These examples are being provided solely to add context and aid in the understanding of the described embodiments. It will thus be apparent to one skilled in the art that the described embodiments may be practiced without some or all of these specific details. In other instances, well known process steps have not been described in detail in order to avoid unnecessarily obscuring the described embodiments. Other applications are possible, such that the following examples should not be taken as limiting.

In the following detailed description, references are made to the accompanying drawings, which form a part of the description and in which are shown, by way of illustration, specific embodiments in accordance with the described embodiments. Although these embodiments are described in sufficient detail to enable one skilled in the art to practice the described embodiments, it is understood that these examples are not limiting; other embodiments may be used, and changes may be made without departing from the spirit and scope of the described embodiments.

Conventional electrocardiogram monitor devices require at least two electrodes to be in physical contact with a user to complete a circuit in order to monitor the electrical activities of the heart of the user. One electrode is often required to be attached near the heart of the user to detect the electric field of the heart. Such arrangement often requires the user to maintain a certain posture. Hence, it can be difficult to continuously conduct electrocardiogram monitoring in a prolonged period because the movement of the user can be severely limited.

Embodiments described herein can relate to cardiac monitor devices that can detect the electrical activities of a heart through a single electrode. An exemplary cardiac monitor device can include an electrode that is configured to be in contact with a limb of a user. The cardiac monitor device can also include an antenna that is capacitively coupled with the body of the user using air as the dielectric. The antenna can serve to replace a second electrode. The electrode can generate a first electrical potential that represents the electrical potential of the limb of the user. The antenna, when capacitively coupled with the body, can generate a second electrical potential that represents the electrical potential of the heart. By determining the potential difference between the electrode and the antenna, the electric field of the heart can be monitored remotely through the antenna.

Since the cardiac monitor device can detect the electric field of the heart with a single physical contact point, the antenna and the electrode can be carried by a single housing. For example, in one case, a small consumer electronic device can include a housing that carries both the antenna, the electrode and circuitry that connects the two components. The consumer electronic device can take the form of an armband that can be worn by the user. The armband can have the capability to wireless communicate with another electronic device such as a smartphone, a tablet, or a smart watch so that the cardiac information can be transmitted and displayed by the other electronic device. In another example, the cardiac monitor device can be a component that is part of a smart watch. Since a single device that is wearable by a user can be used to monitor the electric field of a heart, the electrical activities of the heart can be monitored continuously in a prolonged period, such as in days or even in months.

An exemplary cardiac monitor device can include detection circuitry that can include the antenna and the electrode. An instrumentation amplifier can be connected to the antenna and the electrode to compare the potential difference from the two components. Since air is the dielectric for the capacitive coupling between the antenna and the body of the user, the capacitance can be relatively weak. Hence, the inherent or parasitic capacitance of the detection circuitry can become comparatively significant. A capacitance neutralization circuit can be added to the detection circuitry to reduce or account for the parasitic capacitance. The capacitance neutralization circuit can include an amplifier connected to a feedback loop of the instrumentation amplifier and can reduce the parasitic capacitance by adjusting the gain of the amplifier.

The electrical signals carrying the potential difference that represents the electrical activities of the heart can also be filtered to remove or reduce the noises in the signals. The detection circuitry of a cardiac monitor device can include a low pass filter to remove any high frequency signals. The detection circuitry can include a high pass filter to remove any direct current. In one case, significant noises can be present in the frequency range of 45 Hz to 60 Hz. A notch filter can be used to specifically remove signals in that frequency range. After being filtered, the electrical signals can be amplified multiple times. In one case, the signals can undergo an amplifier with a gain of 100 or so. The amplified signals can be filtered again to further remove the noises in the signals. The signals can then be digitalized and be presented in an electronic device as electrocardiographic information.

These and other embodiments are discussed below with reference to FIGS. 1-11; however, those skilled in the art will readily appreciate that the detailed description given herein with respect to these figures is for explanatory purposes only and should not be construed as limiting.

Figure 1:
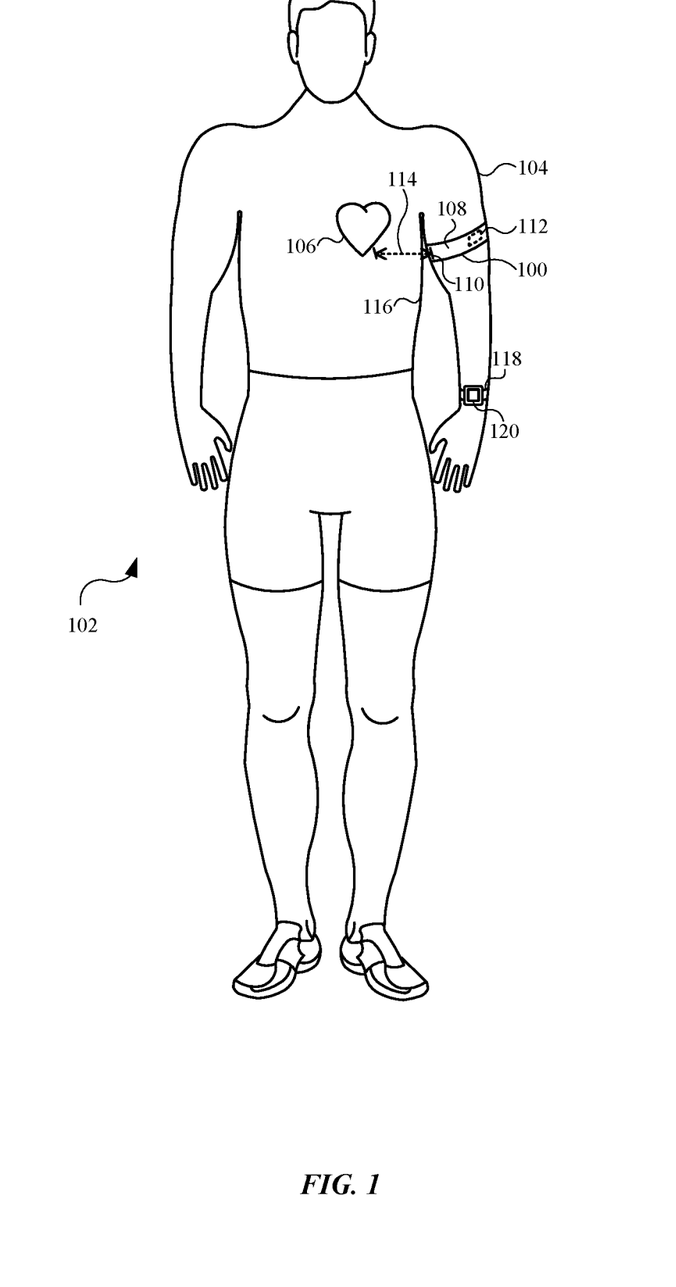
FIG. 1 illustrates a cardiac monitor device wearable by a user, in accordance with some embodiments.

FIG. 1 illustrates an exemplary cardiac monitor device 100, in accordance with some embodiments. A cardiac monitor device can take different forms, including a wearable device that can be removably coupled to a user's appendage. In the particular case shown in FIG. 1, cardiac monitor device 100 can take the form of an armband that can be removably coupled to a user 102. While cardiac monitor device 100 is shown as being worn at upper arm 104 of user 102, cardiac monitor device 100 can also be worn at other locations of user 102, including, but not limited to, the wrist, leg, neck, or body. Also, while cardiac monitor device 100 is shown as a band in FIG. 1, cardiac monitor device 100 can take any other suitable form. Cardiac monitor device 100 can sometimes simply be referred to as a device or a monitor device.

Cardiac monitor device 100 can include a housing 108 that can carry circuitry and electronic components that can detect the electrical activities of the heart 106 of user 102. The circuitry can include at least an antenna 110 and an electrode 112. In some cases, cardiac monitor device 100 is limited to a single electrode 112. Electrode 112 can be configured to come into contact with a location of the skin of user 102 such as at upper arm 104 to measure a first electrical potential at the location. For example, if housing 108 takes the form of a band, electrode 112 can be an exposed piece of metal or a metallic terminal that can be located on the interior facing surface of the band so that electrode 112 is in direct physical contact with the skin of upper arm 104 when user 102 wears cardiac monitor device 100. Antenna 110 can be configured to be positioned across an air gap 114 from the upper body 116 of the user 102. Antenna 110 can be capacitively coupled with heart 106 using the air gap 114 (i.e. air) between antenna 110 and upper body 116 of user 102 as the dielectric. Based on the coupling, antenna 110 can generate a second electrical potential. As such, cardiac monitor device 100 can monitor the electrical activities of heart 106 based on the two electrical potentials detected.

In some embodiments, cardiac monitor device 100 can wirelessly communicate with a portable electronic device 118 using any suitable wireless protocol such as Bluetooth® or WiFi®. Cardiac monitor device 100 can transmit the measured signals carrying information of the potential difference to portable electronic device 118 for further analysis, storage, Internet transmission, and/or display on display assembly 120 of electronic device 118 as visual content. The display of the electrical activities of heart 106 on display assembly 120 can take the form of an electrocardiograph. While electronic device 118 is shown as a wearable electronic device such as a wrist-worn electronic device, electronic device 118 can also take the form of smart phones, tablets or computers.

In some cases, cardiac monitor device 100 can itself be a smart device that includes data processing capability, display assembly, and Internet capability. In those cases, cardiac monitor device 100 can process and display the measured data of the cardiac information, such as heart rates and electrocardiograms. Cardiac monitor device 100 can further share the measured data to electronic device 118. In one particular case, cardiac monitor device 100 can itself be a wrist worn electronic device such as an electronic wrist watch. Instead of being worn at the upper arm, cardiac monitor device 100 can be worn at the wrist. Alternatively, cardiac monitor device 100 that takes the form of a wrist watch can have a flexible band that can be worn at either an upper arm or a wrist. The capacitance between heart 106 and antenna 110 can be inversely related to the distance between heart 106 and antenna 110. Since heart 106 can have a weak electric field, antenna 110 should be positioned at a close distance from heart 106. Preferably cardiac monitor device 100 can be positioned at the upper arm of user 102 because the upper arm is in proximity to heart 106, regardless of the movement of user 102. However, other locations, such as the wrist, is also possible for cardiac monitor device 100.

Figure 2:
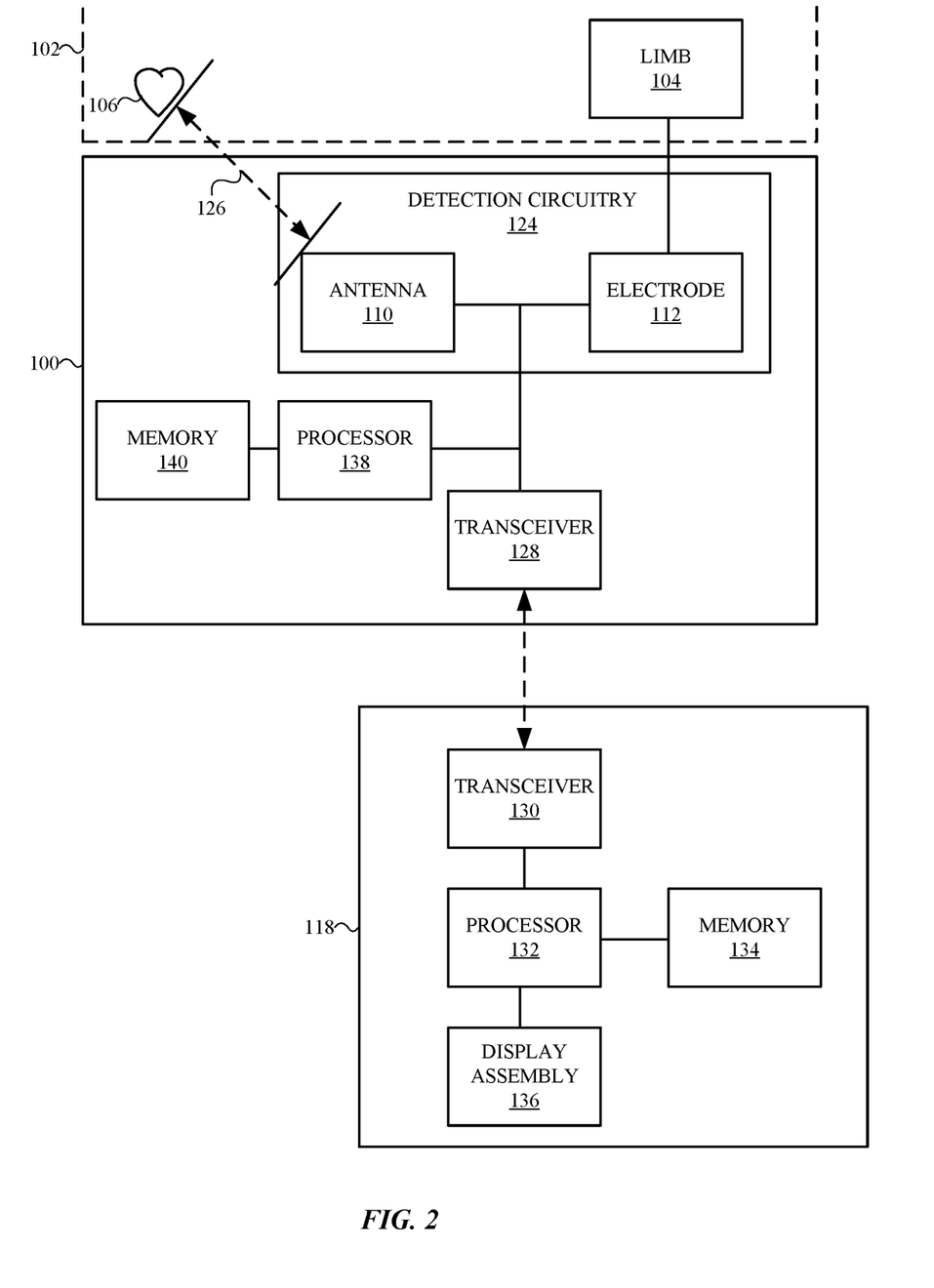
FIG. 2 illustrates a box diagram representing a cardiac monitor system, in accordance with some embodiments.

FIG. 2 is a system schematic box diagram of a system for displaying real time cardiac information of a user, in accordance with some embodiments. The dash lined box represents user 102 including his/her heart 106 and limb 104. Cardiac monitor device 100 can include a detection circuitry 124 that can include antenna 110 and electrode 112. Electrode 112 that can directly measure a first electrical potential of user 102 at limb 104. Antenna 110 can form a capacitor 126 with heart 106 through capacitive coupling. Through determining and amplifying the potential difference between the first electrical potential and the second electrical potential, detection circuitry 124 can generate signals or data representing the electrical activities of heart 106. Cardiac monitor device 100 can optionally include an analog-to-digital convertor capable of digitalizing the potential difference before the signals are transmitted or stored in a memory as digitized data. Cardiac monitor device 100 can include an output that can transmit signals carrying information of the potential difference to an external circuit. The output can take various forms. In one case, the output can be a transceiver 128.

The external circuit can be carried by a portable electronic device. For example, cardiac monitor device 100 can be paired with electronic device 118 so that signals or data representing the electrical activities of heart 106 can be transmitted from transceiver 128 to transceiver 130 of electronic device 118. Electronic device 118 can include processor 132 that can analyze the signals and data. In some cases, processor 132 can also issue a command to control cardiac monitor device 100. The command can be transmitted from transceiver 130 to transceiver 128 to control cardiac monitor device 100. Processor 132 can also generate signals that can represent potential differences between electrode 112 and antenna 110, which can represent the electrical activities of heart 106. Electronic device 118 can include a memory 134 capable of storing data. Processor 132 can cause the data values of the signals saved in the memory 134 as historical data of the electrical activities of heart 106. Processor 132 can also retrieve historical data of heart activities of user 102 from memory 134 to compare the historical data to the real time data. Electronic device 118 can also include a display assembly 136 that can present cardiac information based on the electrical activities of heart 106 analyzed by processor 132. Controlled by processor 132, display assembly 136 can present the electrical activities of heart 106 in a form of electrocardiograph. In other words, display assembly 136 can display signals sent from cardiac monitor device 100 as visual content. The visual presentation of cardiac information can take the form of heart rate, electrocardiography, and/or other suitable presentations. Processor 132 can provide analysis of a user's health condition based on the cardiac information and/or based on the current electrical activities of heart 106 compared to historical data of heart 106. Processor can in turn cause display assembly 136 to issue a notification regarding the electrical activities of heart 106 based on the analysis.

In some embodiments, cardiac monitor device 100 can optionally include a processor 138 that can analyze the potential difference between antenna 110 and electrode 112. Processor 138 can perform the activities that are the same as processor 132. Cardiac monitor device 100 can also optionally include memory 140 that can store historical data of the electrical activities of heart 106.

Figure 3:
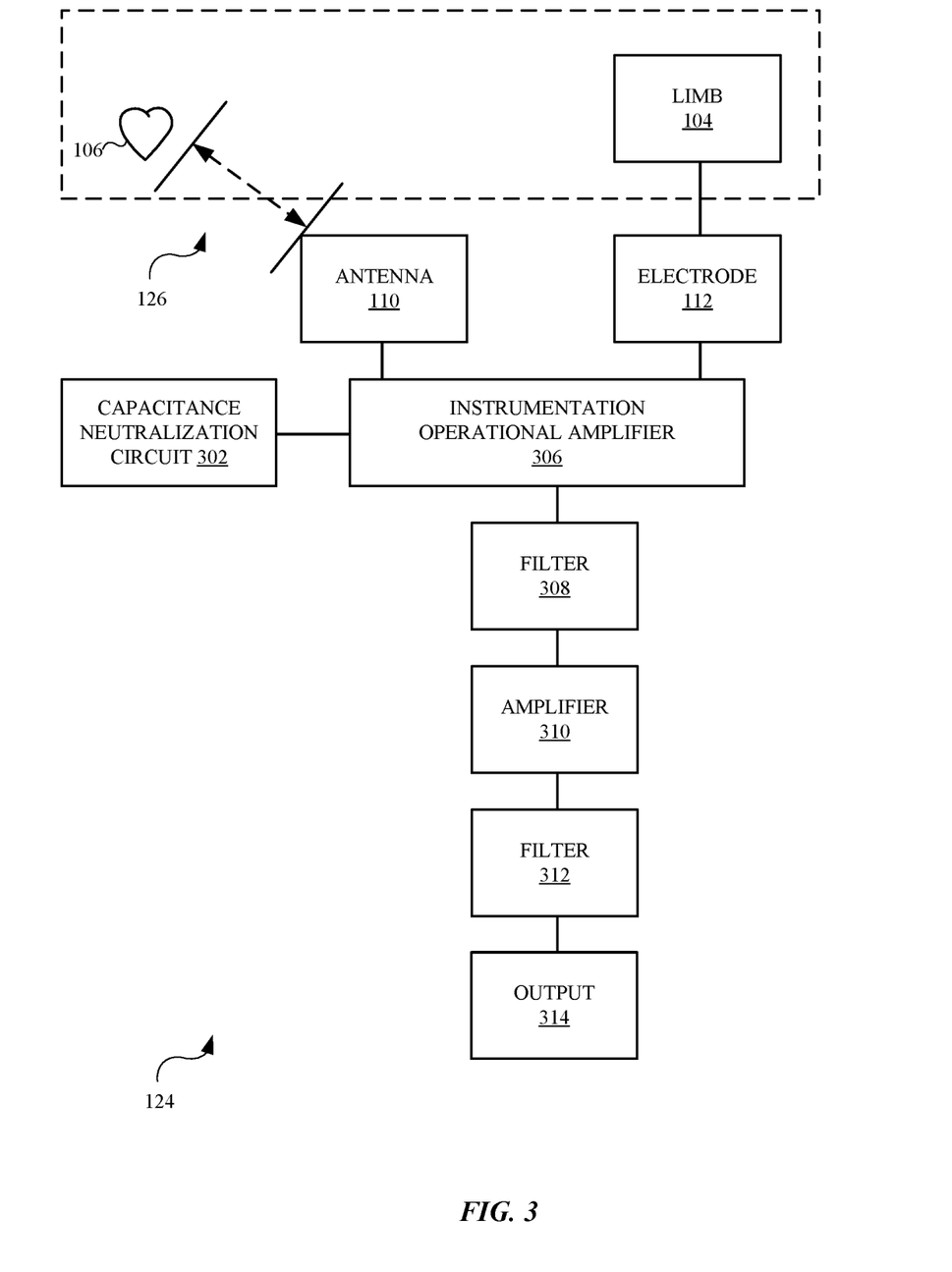
FIG. 3 illustrates a box diagram representing a detection circuitry of a cardiac monitor device, in accordance with some embodiments.

FIG. 3 illustrates a schematic box diagram of detection circuitry 124, in accordance with some embodiments. While FIG. 3 illustrates an exemplary component arrangement in the circuitry, it is understood that some of the components can be optional. Also, the order of some of the components can be changed. Detection circuitry 124 can include electrode 112 that can detect a first electrical potential of limb 104. In one case, first electrical potential of limb 104 can serve as the reference potential of detection circuitry 124, which can be treated as the ground of detection circuitry 124. Detection circuitry can also include antenna 110 that is capacitively coupled with the heart 106 of user 102 to form capacitor 126 to generate a second potential. Since the capacitance generated can have a small value (e.g. in the magnitude of pico-Farad or even femto-Farad), the parasitic capacitance of the circuitry 124 can have a comparatively significant magnitude. Hence, a capacitance neutralization circuit 302 can be coupled to detection circuitry 124 to remove or minimize the effect of parasitic capacitance. Capacitance neutralization circuit 302 can sometimes be referred to as a parasitic capacitance reduction unit.

Detection circuitry 124 can include an instrumentation amplifier 306 that can compare the potential difference between the first potential and the second potential. Instrumentation amplifier 306 can be a type of differential amplifier circuit that can mainly serve to determine the potential difference between electrode 112 and antenna 110. The difference can also optionally be amplified based on the gain of instrumentation amplifier 306. However, in one case, the amplification can be performed in a more downstream component. In such case, instrumentation amplifier 306 can have a gain of 1. It should be understood that other value of the gain of instrumentation amplifier 106 is also possible.

After the potential difference is determined, the electrical signal can undergo a filter circuit 308 that can include one or more filters that filter different frequencies of electrical signals. Typical bio-potential of electrocardiogram signals can have a frequency range of 0.05 Hz to 150 Hz and signal amplitude range from 0.1 mV to 5 mV. The detection of the electrical activity of a heart can be subject to different sources and levels of noises. One potential significant source of noise is from electromyogram, which can have a frequency range of 25 Hz to 3060 Hz and signal amplitude that can be significantly stronger than the signals of electrocardiogram. Electromyogram can have a noticeable overlap in frequency with electrocardiogram in the range of 45 Hz to 60 Hz. Another potential significant source of noise is any alternating current and any coupling with alternating currents. A typical alternating current can have a frequency range of 50 Hz to 60 Hz and significantly stronger signals. Hence, in one embodiment, filter circuit 308 can allow signals with frequency range of 0.5 Hz to 40 Hz to pass. By using such frequency range, detection circuitry 124 can target a significant portion of typical frequency range of electrocardiogram signals that does not significantly overlap with electromyogram or alternating currents.

Filter circuit 308 can include a high pass filter that can eliminate low frequency electrical signals that are below the lower bound of the target frequency range of filter circuit 308. The high pass filter can reduce or eliminate any unwanted direct currents in detection circuitry 124. Filter circuit 308 can also include a low pass filter that can eliminate electrical signals with frequencies that are higher that the upper bound of the target frequency range of filter circuit 308. The low pass filter can reduce or eliminate any unwanted alternating currents and other noises in detection circuitry 124. Since the frequency range of 45 Hz to 60 Hz can present different sources of noises, filter circuit 308 can additionally include a notch filter that specifically removes frequency range of 45 Hz to 60 Hz.

After the electrical signals are filtered by filter circuit 308, the electrical signals, which can solely or at least mainly represent the potential difference between antenna 110 and electrode 112, can be amplified by amplifier 310. Amplifier 310 can be any suitable amplifier such as an operational amplifier based multiplier. The multiplier can be inverting or non-inverting. Since the bio-potential detected can have a small value (in the range of 0.1-5 mV), the amplification can be in ten or hundred folds. In one particular embodiment, amplifier 310 can have a gain of 100.

After the amplification, the electrical signals at the output of amplifier 310 can be filtered again by a second filter circuit 312. Since amplifier 310 can have a high gain, any residual noise may also be amplified along with the targeted potential difference. Hence, second filter circuit 312 can filter the amplified signals one more time to retain only the amplified signals at the target frequency range. Again, similar to first filter circuit 308, second filter circuit 312 can include one or more high pass filter, law pass filter, and notch filter.

The amplified and filtered signals after amplifier 310 and the filters 308 and/or 312 can be transmitted to output 314. Output 314 can be connected to a processor of cardiac monitor device 100 for analysis or to a transmitter of cardiac monitor device 100 to send out the signals to an electronic device for processing and storage. Output 314 can transmit signals carrying information of the potential difference to another component or another device.

Figure 4A:
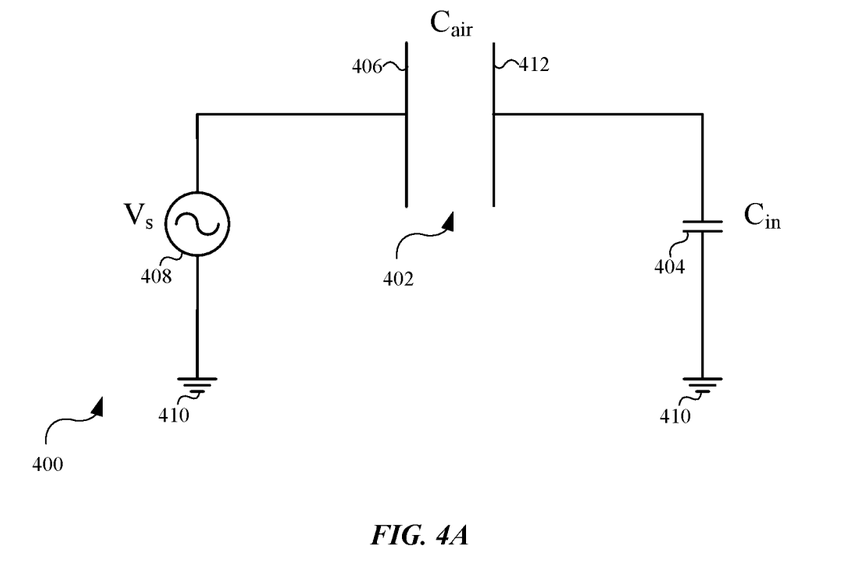
FIG. 4A illustrates a capacitor circuit, in accordance with some embodiments.

FIG. 4A illustrates a capacitor circuit 400 that illustrates the principle of one exemplary implementation of how antenna 110 and electrode 112 determine the electrical activity of heart 106, in accordance with some embodiments. Capacitor circuit 400 can include a first capacitor 402 and a second capacitor 404 connected in series. First capacitor 402 can have two metal plates that are separated by air. Hence, first capacitor 402 can have a capacitance of $C_{air}$, which can depend on the permittivity of air. A first metal plate 406 of first capacitor 402 can be connected to an electric field source 408 relative to a reference level 410. A second metal plate 412 of first capacitor 402 can be connected to second capacitor 404. Second capacitor 404 can have a capacitance $C_{in}$. Second capacitor 404 is also connected to the same reference level 410. For an alternating circuit, the impedance of a capacitance is equal to the inverse of jwC, wherein w is the frequency of the electrical current and C is the capacitance of the capacitor. Since first capacitor 402 and second capacitor 404 are connected in series, equation (1) below can represent the relationship between the electrical potential $V_s$ of electric field source 408 and the electrical potential $V_{in}$ at second capacitor 404.

$$V_{in} = [(1/jwC_{in})/(1/jwC_{in} + 1/jwC_{air})] \times V_s \qquad \text{Eq. (1)}$$

By simplifying equation (1), the relation of $V_{in}$ and $V_s$ can be represented by equation (2) below.

$$V_{in} = V_s \times \frac{C_{air}}{C_{air} + C_{in}} \qquad \text{Eq. (2)}$$

Figure 4B:
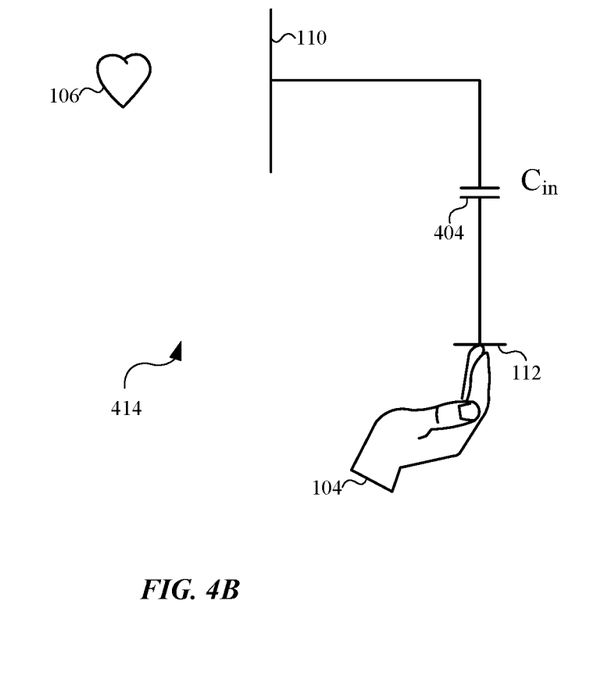
FIG. 4B illustrates a second capacitor circuit, in accordance with some embodiments.

Now referring to FIG. 4B, in accordance with some embodiment, a second capacitor circuit 414, which can be equivalent to the general arrangement of capacitor circuit 400, can be constructed using antenna 110 and electrode 112 to detect the electrical potential of heart 106, which can be equivalent to the electric field source 408. First capacitor 402 can be replaced by antenna 110 that is capacitively coupled with heart 106. Second capacitor 404 can remain in second capacitor circuit 414 and can be connected to electrode 112, which can serve as reference level 410. In other words, since electrode 112 is configured to be in physical contact of limb 104, the electrical potential of limb 104 is the equivalent of the reference level 410 in FIG. 4A. It should be noted that while limb 104 in FIG. 4B is represented by a hand, electrode 112 can be in contact with other location of the body such as an upper arm. The electrical potential of heart 106 relative to electrical potential of limb 104 (i.e. the potential difference between heart 106 and limb 104) can be $V_s$ in this system. $V_s$ can be determined by $V_{in}$ using the equation (2). In other words, the electrical activity of heart 106 can be determined by capacitor circuit 414 using antenna 110 that capacitively couples with heart 106 and electrode 112 that can be configured to be in contact with a part of the user's body. In one case, antenna 110, capacitor 404, and electrode 112 can be connected in series.

Figure 5:
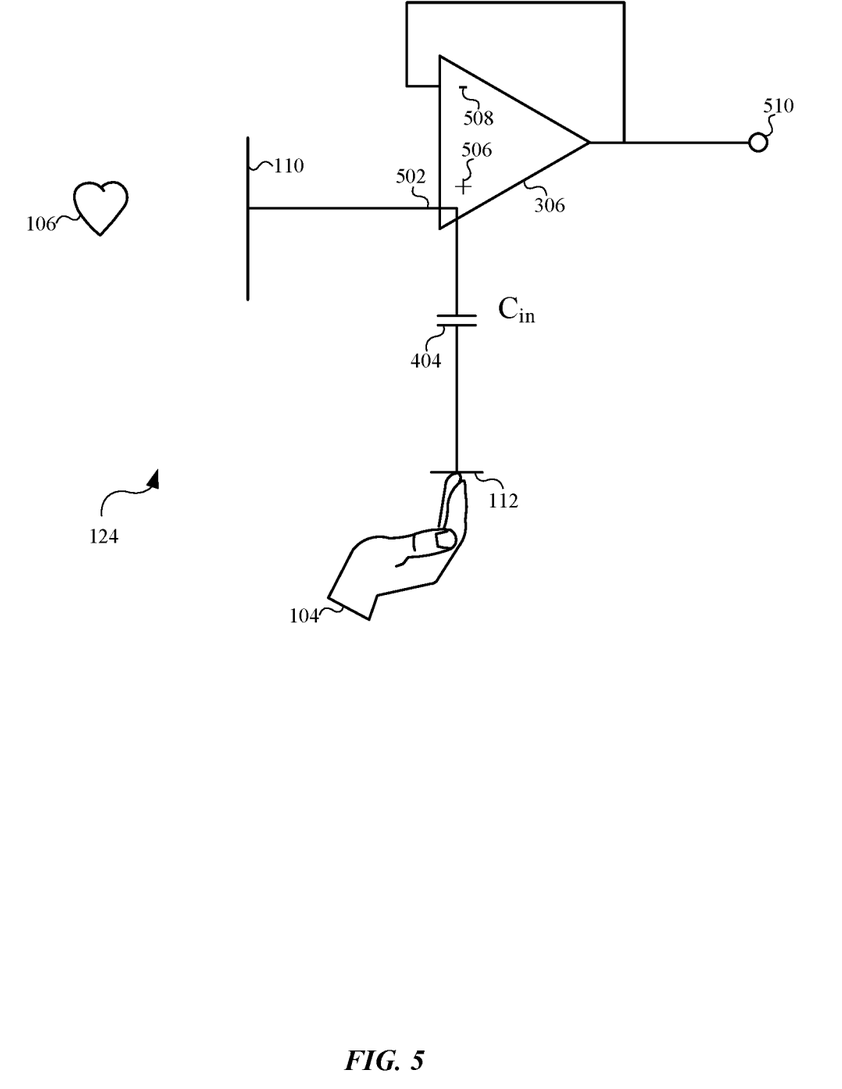
FIG. 5 illustrates a detection circuit that can detect the electrical potential of a heart, in accordance with some embodiments.

FIG. 5 illustrates a portion of detection circuitry 124, in accordance with some embodiments. An exemplary instrumentation amplifier 306 can be added to point 502 of circuit 414 shown in FIG. 4B in accordance with some embodiments. In one case, capacitor 404 may not be a separate capacitor added to detection circuitry 124. Instead, capacitor 404 may represent the inherent capacitance (or parasitic capacitance) of instrumentation amplifier 306. Instrumentation amplifier 306 can have its non-inverting input terminal 506 connected to point 502. It should be noted that point 502 can have the potential $V_{in}$ relative to electrode 112. Operational amplifier 306 can have its inverting input terminal 508 connected to its output 510 in a feedback loop. Hence, operational amplifier 306 can serve as a unity gain buffer that can measure the potential $V_{in}$ at point 502 and that can output such potential. Operational amplifier 306 can output $V_{in}$ for further processing so that the potential of heart 106 relative to electrode 112 can be determined based on Equation (2). In some cases, operational amplifier 306 can also include resistors (not shown) of different values at the feedback loop so that operational amplifier 306 can also serve as a multiplier to amplify $V_{in}$.

Figure 6:
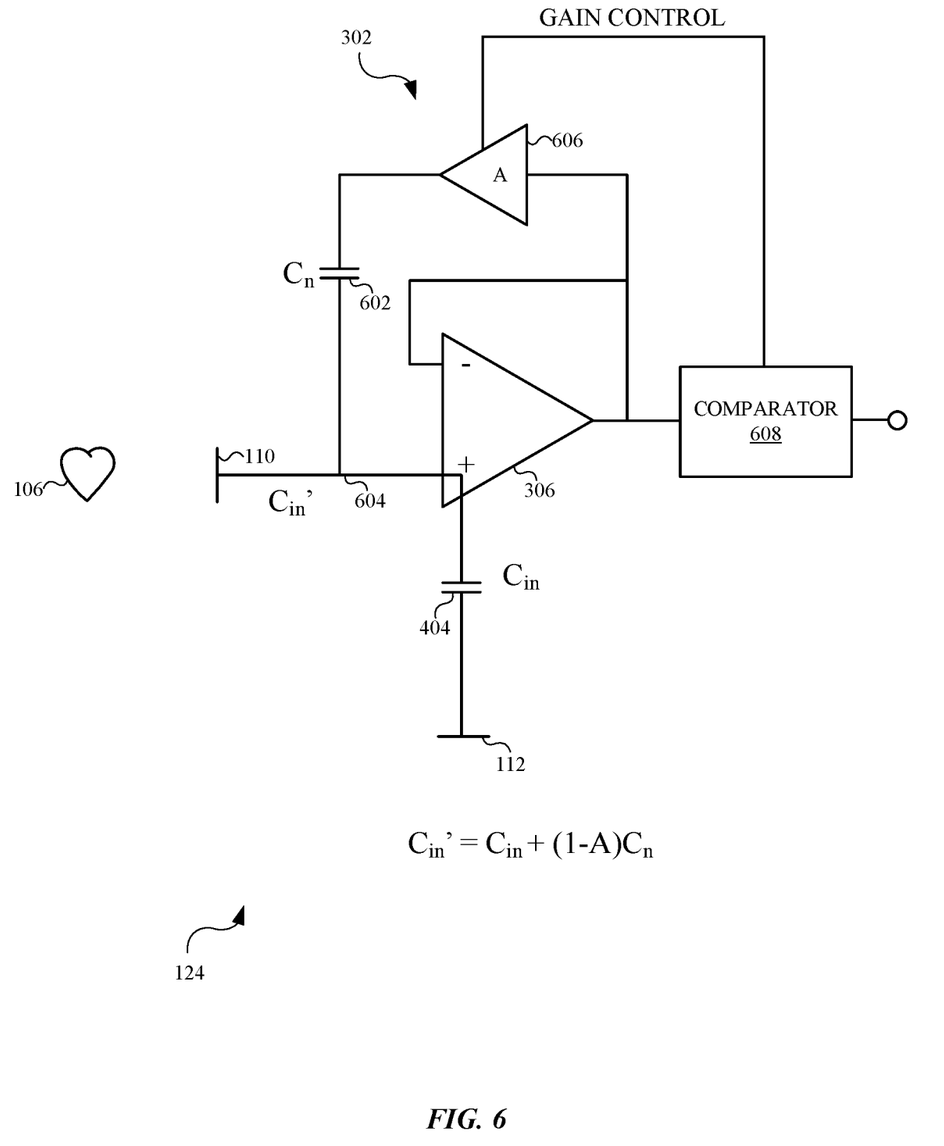
FIG. 6 illustrates a capacitance neutralization circuit, in accordance with some embodiments.

FIG. 6 illustrates a portion of detection circuitry 124, in accordance with some embodiments. An exemplary capacitance neutralization circuit 302 can optionally be added to detection circuitry 124 to reduce the parasitic capacitance of detection circuitry 124. This particular embodiment of detection circuitry 124 can be constructed based on the circuit shown in FIG. 5. As explained above, capacitor 404 may represent the parasitic capacitance of instrumentation amplifier 306 or the parasitic capacitance of the system. Referring to equation (2), which is reproduced below, yin can have a value that is smaller than $V_s$ because the denominator of equation (2) is equal or larger than the numerator.

$$V_{in} = V_s \times \frac{C_{air}}{C_{air} + C_{in}} \quad \text{Eq. (2)}$$

It should be noted that $V_s$ can have a relative small value because $V_s$ can represent the biopotential of heart 106. The parasitic capacitance of the system, Cm, can have a relatively large value compared to capacitance of air, Can, which can be in the magnitude of pico-Farad or even femto-Farad. If the parasitic capacitance of the system, Cm, is large, it can significantly reduce the value of yin according to Equation (2).

A capacitance neutralization circuit 302 can be added to reduce the effect of the parasitic capacitance of the system so that the detected value of yin can be maximized. A capacitor 602, having a capacitance $C_n$, can be added to the circuit and can reduce the effect of parasitic capacitance of detection circuitry 124. The capacitor 602 can connect the non-inventing input terminal of instrumentation amplifier 306 and the output of instrumentation amplifier 306 at point 604 to form a feedback loop. An amplifier 606 with gain A can be connected to capacitor 602. The overall capacitance of the system, $C_{in}'$, can be reduced based on Equation (3) below.

$$C_{in}' = C_{in} + (1-A)C_n \quad \text{Eq. (3)}$$

By adjusting the gain of amplifier 606 and the value of the capacitance $C_n$ of capacitor 602, the overall capacitance of $C_{in}'$ of the system can be reduced. For example, in one case, the actual parasitic capacitance $C_{in}$ can be estimated and capacitor 602 can have the capacitance value $C_n$ equal to the estimated value of Cm. The gain of amplifier 606 can be set to 2. Hence, ideally the overall capacitance of $C_{in}'$ of the system can be zero or can at least be minimized. When the overall capacitance of $C_{in}'$ of the system is reduced, yin can be maximized according to Equation (4) below.

$$V_{in} = V_s \times \frac{C_{air}}{C_{air} + C_{in}'} \quad \text{Eq. (4)}$$

The capacitance neutralization circuit 302 can also include a comparator 608 that can compare the output of instrumentation amplifier 306 to a reference signal. Based on the comparison results, comparator 608 can control the gain of amplifier 606. By dynamically adjusting the gain A of amplifier 606 to minimize the value of CZ, the effect of parasitic capacitance of the system can be minimized.

Figure 7:
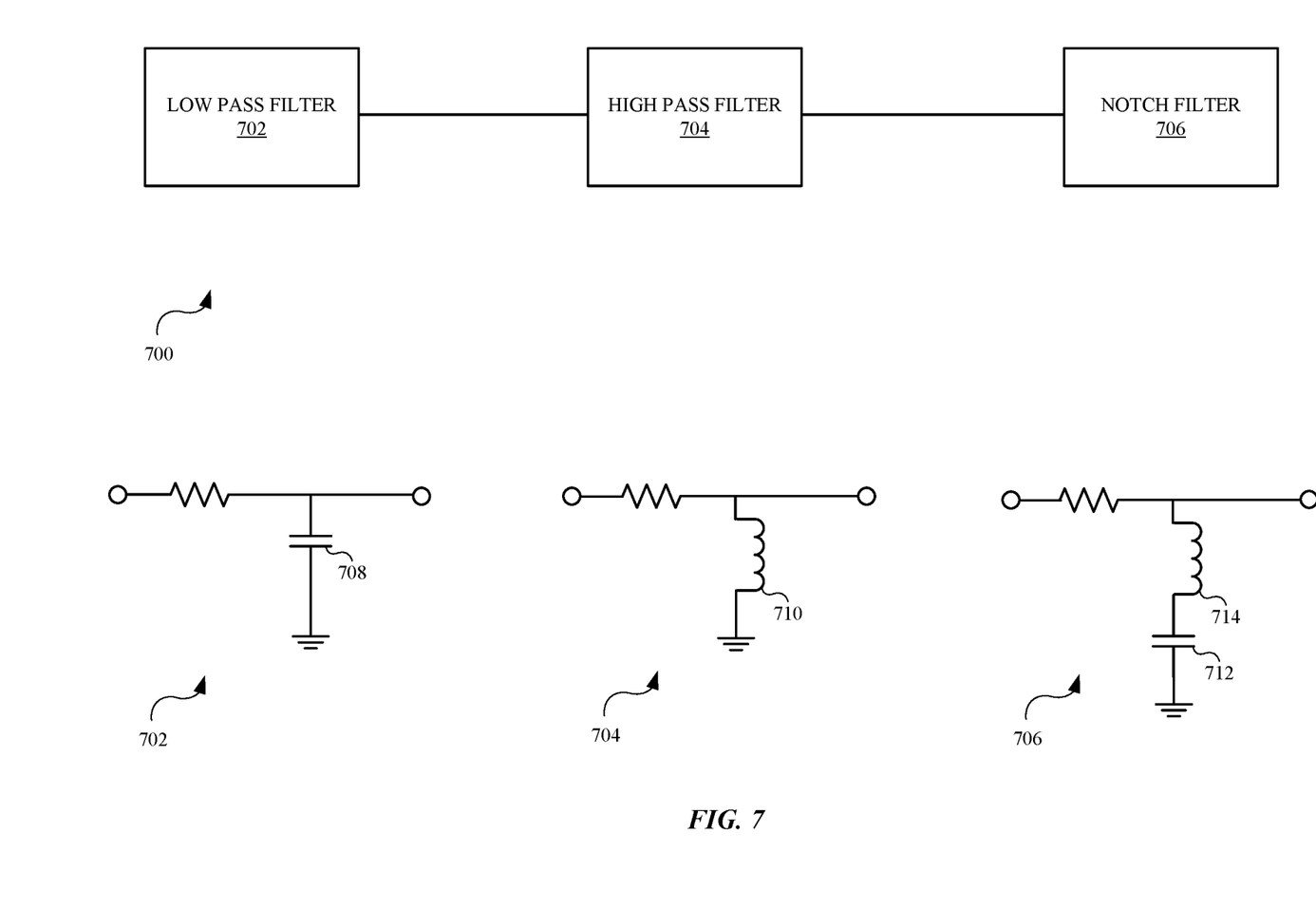
FIG. 7 illustrates a filter circuit, in accordance with some embodiments.

FIG. 7 illustrates a filter circuit 700, in accordance with some embodiments. After instrumentation amplifier 306 outputs electrical signals that can represent $V_{in}$ or amplified $V_{in}$, the electrical currents can undergo one or more filters that can remove or attenuate components of the signals that are not in the targeted frequency range. Filter circuit 700 can be an exemplary filter circuit that can be used as the filter circuit 308 and/or 312. It should be noted that the arrangement of filter circuit 700 is exemplary only and the exact configuration of filter circuits 308 and 312 can vary. Also, one or more components shown in filter circuit 700 can be optional. Filter circuit 700 can include a low pass filter 702, a high pass filter 704, and a notch filter 706. The three filters can be arranged in any order.

Low pass filter 702 can include a capacitor 708 that can be connected to ground. Capacitor 708 can be connected to the main signal path in parallel. Capacitor 708 can have low impedance at high frequency so that signals with high frequency can be removed/attenuated. In one case, signals with frequency of 45 Hz or above can be removed/attenuated.

High pass filter 704 can include an inductor 710 that can be connected to ground. Inductor 710 can be connected to the main signal path in parallel. Inductor 710 can have low impedance at low frequency so that signals with low frequency can be removed/attenuated. In one case, signal with frequency of 0.5 Hz or below can be removed/attenuated.

Notch filter 706 can be used to remove signals at a certain specific frequency range. Notch filter 706 can include a capacitor 712 and an inductor 714 that can be connected in series. Capacitor 712 and inductor 714 combined can be connected to the main signal path in parallel. Capacitor 712 and inductor 714 combined can have low impedance at a specific frequency range based on the relative value of the capacitance of capacitor 712 and the inductance of inductor 714. In some cases, since signals with frequency of 45 Hz to 60 Hz can include significant noises from different sources, notch filter 706 can specifically remove/attenuate components of the signals in such frequency range.

Figure 8:
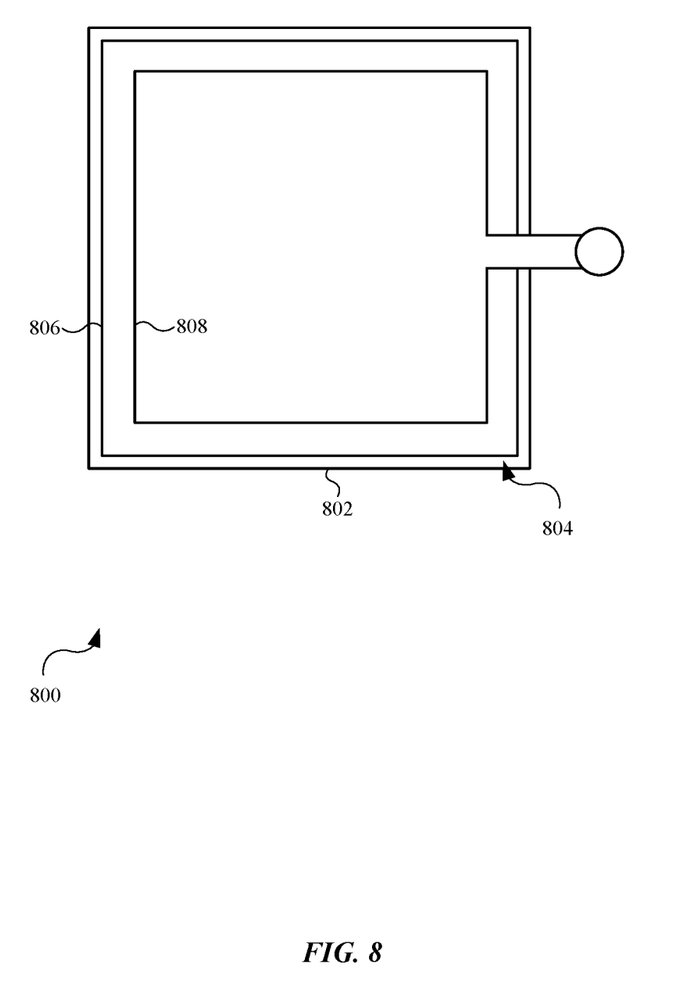
FIG. 8 illustrates a plan view of an electrode, in accordance with some embodiments.

FIG. 8 is a plan view of an exemplary electrode 800, in accordance with some embodiments. Electrode 800 can be used as the electrode 112. Electrode 800 can include a surface 802 and a metal moat 804 that can surround surface 802 of electrode 800. Metal moat 804 can be used as a shield to isolate noise from coupling to electrode 800. Electrode 800 can be a metallic plate. Metal moat 804 can include an outer wall 806 that can generally surround an inner wall 808. Inner wall 808 can be connected to the main detection circuitry while outer wall 806 can be connected to ground. In one case, both outer wall 806 and inner wall 808 can protrude from the surface 802. Metal moat 804 can serve as a shield to remove the noise level of the cardiac monitor device in a manner similar to co-axial cable. Similar metal moat can also implemented for any antenna of a cardiac monitor device, such as antenna 110.

Figure 9:
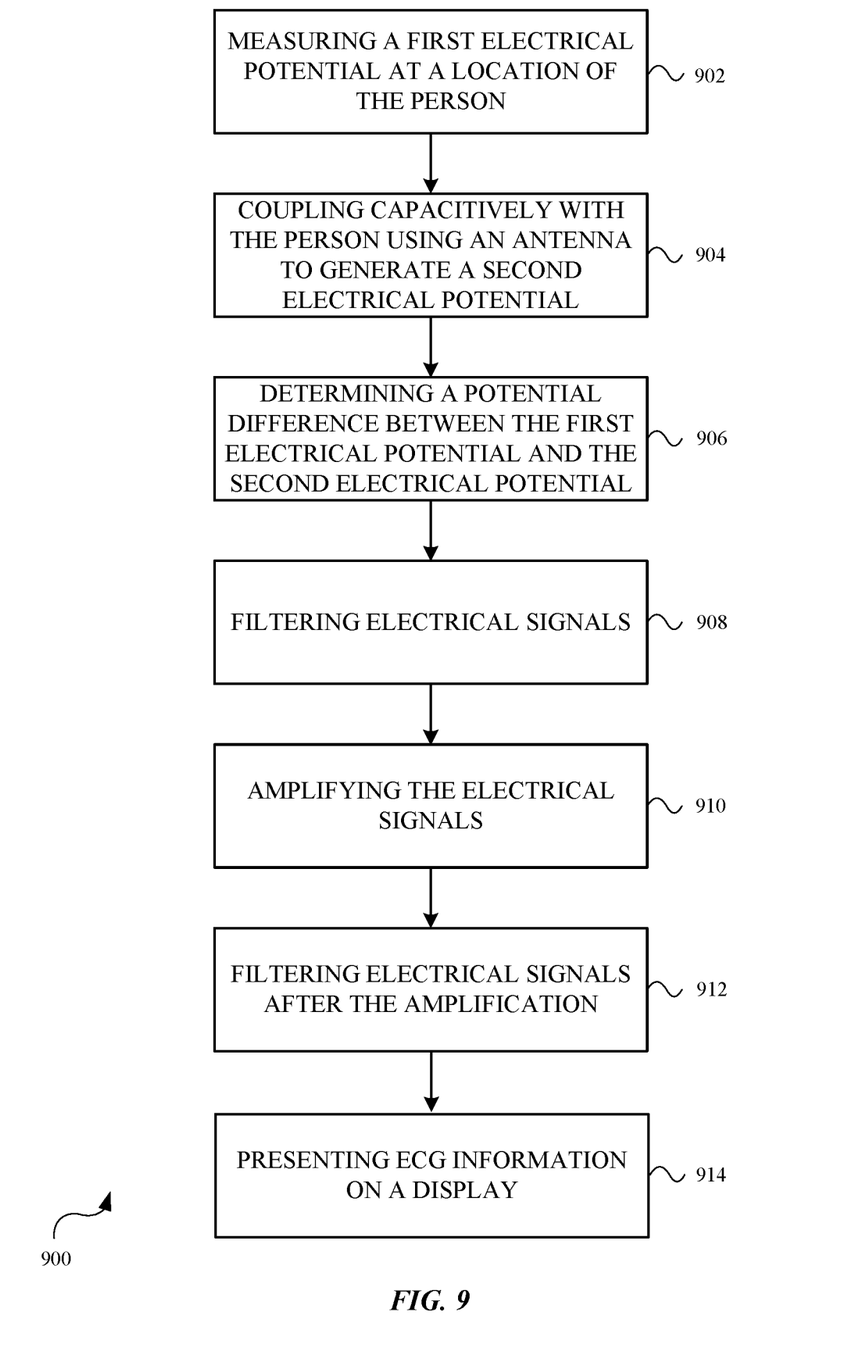
FIG. 9 illustrates a flowchart depicting a method for monitoring cardiac information of a person, in accordance with some embodiments.

FIG. 9 is a flowchart depicting a method 900 for monitoring cardiac information of a person, in accordance with some embodiments. The method 900 can be performed, at least in part, by one or more of the cardiac monitor device 100 or the portable electronic device 118. At step 902, the method can include measuring a first electrical potential at a location of the person. The location can be a location of a limb of the person. An electrode can be configured to be physically in contact with the person to measure the first electrical potential. At step 904, the method can include coupling capacitively with the person using an antenna to generate a second electrical potential. The antenna can also be located at the limb of the person. At step 906, the method can include determining a potential difference between the first electrical potential and the second electrical potential. The potential difference can represent the electrical activity of the heart of the person. At step 908, the method can include filtering the electrical signals that carry the information of the potential difference. Signals with frequencies that are beyond the targeted frequency range (such as a certain range of typical ECG signals) can be filtered. At step 910, the method can include amplifying the signals. The gain of the amplification can vary. In one case, the gain can be 100. At step 912, the amplified signals can be filtered again to ensure a vast majority, if not all, of noise can be filtered and removed. The filtered signals can represent the electrocardiogram information of a user. At step 914, the method can include presenting ECG information on a display.

Figure 10:
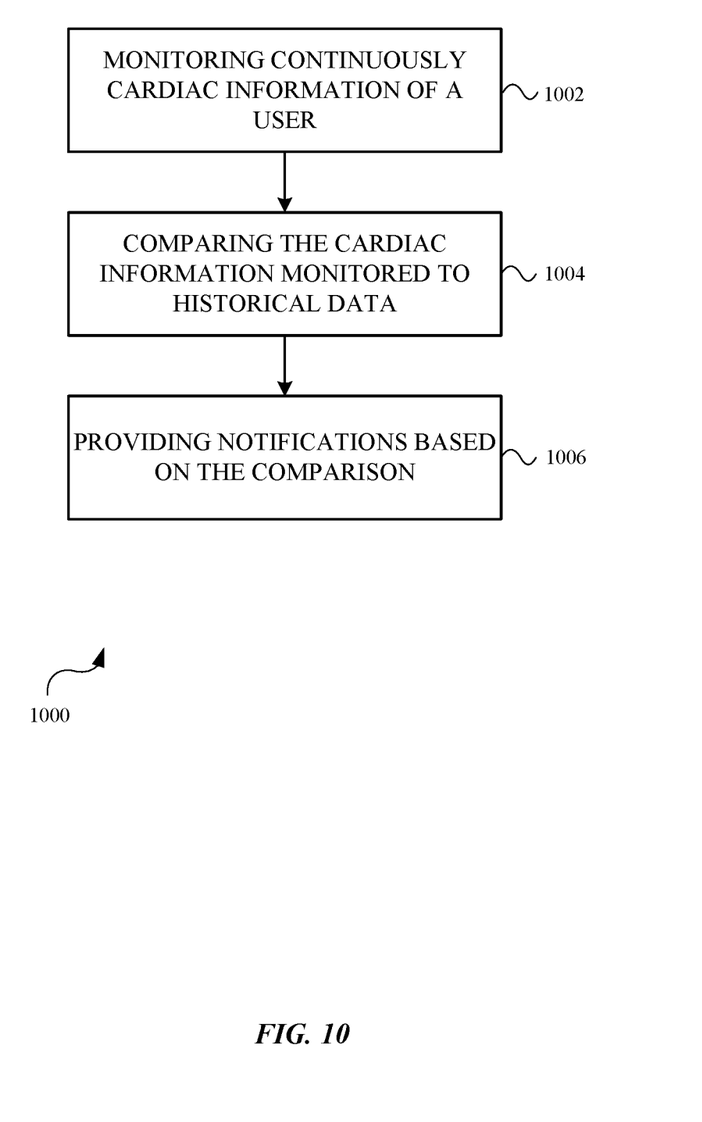
FIG. 10 illustrates a flowchart depicting a method for monitoring the activity of heart of a person, in accordance with some embodiments.

FIG. 10 is a flowchart depicting a method 1000 for monitoring the activity of the heart of a person, in accordance with some embodiments. Since only a single electrode is needed to detect the cardiac information of a person using a cardiac monitor device that can take the form of a wearable device such as an armband, the activity of the heart can be monitored in a prolonged period continuously (such as continuously over days or even months). At step 1002, the method can include monitoring, continuously, the cardiac information of a user, such as by detecting a potential difference between the heart and a limb of the user. The step can also include digitalizing the potential difference as digitalized data and storing the digitalized data in a memory. Step 1002 can include issuing and transmitting a command from a portable electronic device to a cardiac monitoring device. The digitized data can then be transmitted from the cardiac monitoring device to the portable electronic device as signals received by a transceiver of the portable electronic device.

At step 1004, the method can include comparing the cardiac information monitored to historical data of the user. A processor of the portable electronic device can perform an analysis of the cardiac information via a comparison with the historical data of the user. At step 1006, the method can include providing notifications and presenting visual content to the user based on the comparison and/or based on the cardiac information. This step can include presenting the potential difference as electrocardiographic visual content. The notifications can be presented on a display of the cardiac monitor device or a display assembly of a portable electronic device that can be paired with the cardiac monitor device. The notifications can also be routine notifications and/or notifications based on specific conditions. For example, a routine notification can be presented once a day to notify the user that his or her heart activity is normal. When an abnormal heart activity (such as an irregular heart beat, faster or slower than usual heart beat) is detected, notifications can be presented to provide warnings to the user. In addition, in response to the user's selection, cardiac information including electrocardiogram and heart beat can also be presented.

Figure 11:
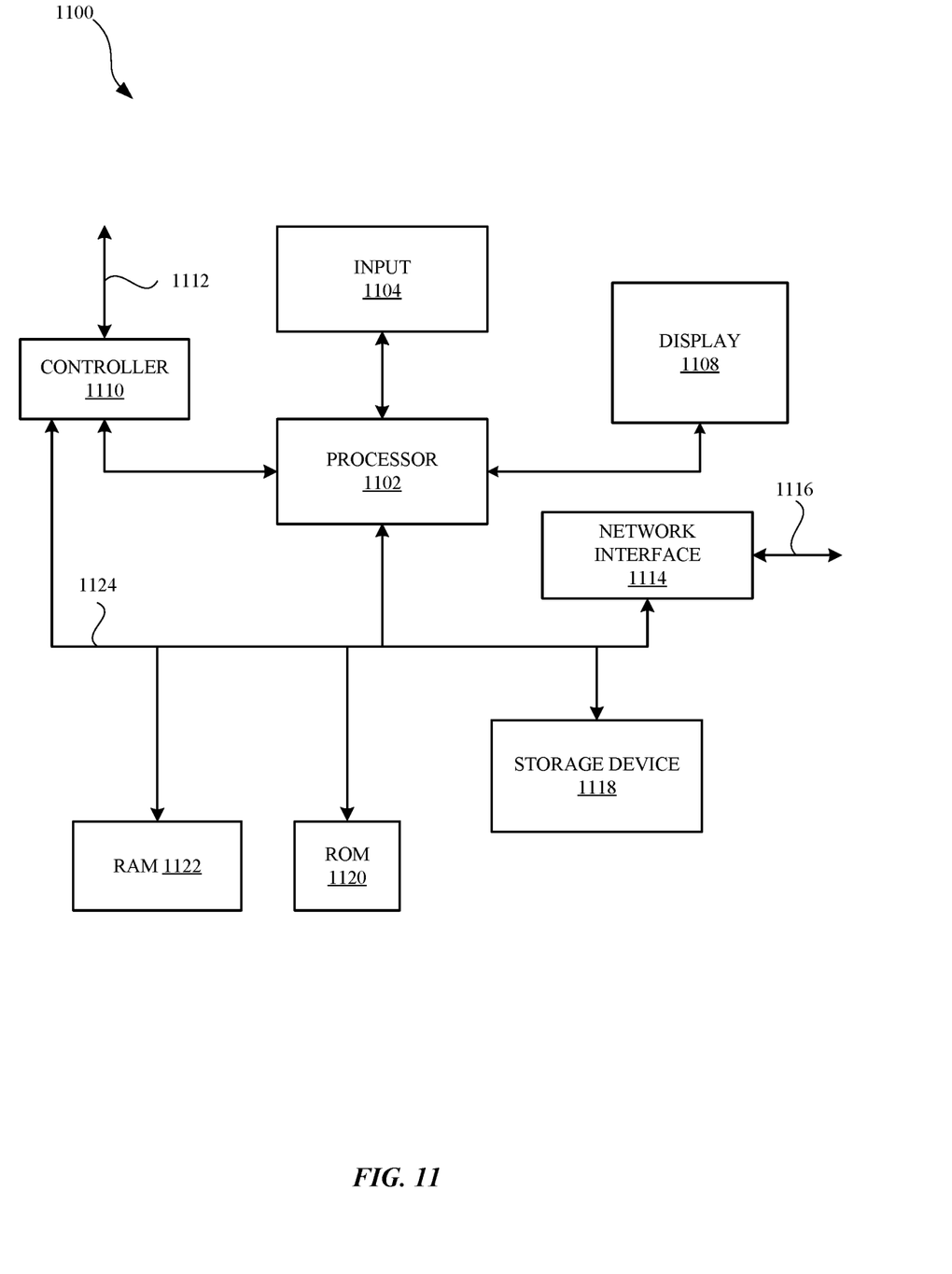
FIG. 11 illustrates a block diagram of an electronic device, in accordance with some embodiments.

FIG. 11 is a block diagram of an electronic device 1100 that can represent the components of cardiac monitor device 100 and/or portable electronic device 118, in accordance with some embodiments. It will be appreciated that the components, devices or elements illustrated in and described with respect to FIG. 11 may not be necessary and thus some may be omitted in certain embodiments. The electronic device 1100 can include a processor 1102 that represents a microprocessor, a coprocessor, circuitry and/or a controller for controlling the overall operation of electronic device 1100. Although illustrated as a single processor, it can be appreciated that the processor 1102 can include a plurality of processors. The plurality of processors can be in operative communication with each other and can be collectively configured to perform one or more functionalities of the electronic device 1100 as described herein. In some embodiments, the processor 1102 can be configured to execute instructions that can be stored at the electronic device 1100 and/or that can be otherwise accessible to the processor 1102. As such, whether configured by hardware or by a combination of hardware and software, the processor 1102 can be capable of performing operations and actions in accordance with embodiments described herein.

The electronic device 1100 can also include user input device 1104 that allows a user of the electronic device 1100 to interact with the electronic device 1100. For example, user input device 1104 can take a variety of forms, such as a button, keypad, dial, touch screen, audio input interface, visual/image capture input interface, input in the form of sensor data, etc. Still further, the electronic device 1100 can include a display 1108 (screen display) that can be controlled by processor 1102 to display information to a user. Controller 1110 can be used to interface with and control different equipment through equipment control bus 1112. The electronic device 1100 can also include a network/bus interface 1114 that couples to data link 1116. Data link 1116 can allow the electronic device 1100 to couple to a host computer or to accessory devices. The data link 1116 can be provided over a wired connection or a wireless connection. In the case of a wireless connection, network/bus interface 1114 can include a wireless transceiver.

The electronic device 1100 can also include a storage device 1118, which can have a single disk or a plurality of disks (e.g., hard drives) and a storage management module that manages one or more partitions (also referred to herein as "logical volumes") within the storage device 1118. In some embodiments, the storage device 1118 can include flash memory, semiconductor (solid state) memory or the like. Still further, the electronic device 1100 can include Read-Only Memory (ROM) 1120 and Random Access Memory (RAM) 1122. The ROM 1120 can store programs, code, instructions, utilities or processes to be executed in a non-volatile manner.

In some case, ROM 1120 can include a non-transitory computer readable storage medium configured to store instructions that, when executed by a processor included in electronic device 1100, cause electronic device 1100 to perform different processes and methods described in accordance with different embodiments. The RAM 1122 can provide volatile data storage, and store instructions related to components of the storage management module that are configured to carry out the various techniques described herein. The electronic device 1100 can further include data bus 1124. Data bus 1124 can facilitate data and signal transfer between at least processor 1102, controller 1110, network interface 1114, storage device 1118, ROM 1120, and RAM 1122.

As described above, one aspect of the present technology is the gathering and use of data available from various sources to improve the delivery to users of health content or any other content that may be of interest to them. The present disclosure contemplates that in some instances, this gathered data may include personal information data that uniquely identifies or can be used to contact or locate a specific person. Such personal information data can include demographic data, location-based data, telephone numbers, email addresses, twitter ID's, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to provide insights into a user's general wellness, or may be used as positive feedback to individuals using technology to pursue wellness goals. Accordingly, use of such personal information data enables users to adjust their exercise routines or lifestyle. Further, other uses for personal information data that benefit the user are also contemplated by the present disclosure. For instance, health and fitness data may be used to provide suggestions to a user for healthy recipes or the location of nearby fitness facilities.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services or anytime thereafter. In another example, users can select not to provide health and fitness data for targeted advertisement delivery services, while providing other personal information data such as location. In yet another example, users can select to limit the length of time health and fitness data is maintained or entirely prohibit the development of a baseline health profile. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the device, or publicly available information.

The various aspects, embodiments, implementations or features of the described embodiments can be used separately or in any combination. The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A wearable device for detecting electrical activities of a heart of a user, the wearable device comprising:
   a housing, the housing carrying:
      an electrode configured to come into contact with a user's skin at a first location on the user's body and configured to measure a reference electrical potential at the first location;
      an antenna configured to be positioned across an air gap between the housing and a second location on the user's body that is different from the first location so that the antenna is capable of being capacitively coupled with the body to generate a second electrical potential;

an amplifier configured to determine a potential difference between the reference electrical potential and the second electrical potential, wherein the potential difference represents the electrical activities of the heart; and an output configured to transmit signals carrying information of the potential difference to an external circuit.

2. The wearable device as recited in claim 1, wherein the external circuit is carried by a portable electronic device having a display assembly capable of displaying the information in a form of electrocardiograph.

3. The wearable device as recited in claim 1, wherein the electrode comprises a metal moat surrounding a surface of the electrode.

4. The wearable device as recited in claim 3, wherein the metal moat comprises an outer wall that is grounded and that surrounds an inner wall.

5. The wearable device as recited in claim 1, wherein the wearable device is wearable at an upper arm of the user.

6. The wearable device as recited in claim 1, wherein the wearable device is limited to a single electrode.

7. The wearable device as recited in claim 1, wherein the housing further carries a parasitic capacitance reduction unit configured to reduce an effect of a parasitic capacitance of the amplifier.

8. The wearable device as recited in claim 7, wherein the parasitic capacitance reduction unit comprises a second amplifier and a capacitor that forms a feedback loop with at a non-inverting input terminal of the amplifier.

9. The wearable device as recited in claim 1, wherein the wearable device is an armband and the electrode is positioned on an interior facing surface of the armband.

10. The wearable device as recited in claim 1, further comprising a filter circuit capable of filtering noise with frequencies that are below 0.5 Hz and that are above 45 Hz.

11. A method carried out by a portable electronic device that is capable of presenting electrocardiographic information of a heart of a user, the portable electronic device having a processor, a wireless transceiver, and a display assembly, the method comprising:

issuing, by the processor, a command to control a cardiac monitor device separated from the portable electronic device, wherein the cardiac monitor device is capable of monitoring electrical activities of the heart through capacitive coupling between an antenna of the cardiac monitor device located at a first location on the user's body and across an air gap to a second location on the user's body that is different from the first location;

transmitting, by the transceiver, the command to the cardiac monitor device;

receiving, by the transceiver, signals from the cardiac monitor device; and presenting, by the display assembly, the electrical activities of the heart as visual content in a form of an electrocardiograph based on the signals.

12. The method as recited in claim 11, wherein the portable electronic device is a wrist-worn electronic device.

13. The method as recited in claim 11, further comprising storing, in a memory of the portable electronic device, data based on the signals from the cardiac monitor device as historical data of the electrical activities of the heart.

14. The method as recited in claim 11, further comprising issuing, by the processor, a notification regarding the electrical activities of the heart based on the signals.

15. The method as recited in claim 11, further comprising performing, by the processor, an analysis of current electrical activities of the heart compared to historical data of the heart.

16. A system for monitoring electrical activities of a heart of a user, comprising:

an electrode configured to come into contact with a user's skin at a first location on a limb of the user;

an antenna configured to be positioned across an air gap between the antenna and a second location on the user's body that is different from the first location so that the antenna is capacitively coupled with the body;

a processor configured to generate a signal representing a potential difference between the electrode and the antenna that indicates the electrical activities of the heart; and a display assembly controlled by the processor and capable of presenting the signal as visual content.

17. The system as recited in claim 16, wherein the electrode and the antenna are carried by a cardiac monitor device and the processor and the display assembly are carried by a portable electronic device, the cardiac monitor device being wearable by the user.

18. The system as recited in claim 17, wherein the cardiac monitor device and the display assembly are capable of communicating with each other wirelessly.

19. The system as recited in claim 16, wherein the electrode, the antenna, the processor, and the display assembly are carried by a wrist-worn electronic device.

20. The system as recited in claim 16, further comprising:

an analog-to-digital convertor capable of digitalizing the potential difference as digitalized data; and a memory capable of storing the digitalized data.

* * * * *